(12) United States Patent
Almqvist

(10) Patent No.: US 6,965,681 B2
(45) Date of Patent: Nov. 15, 2005

(54) ARRANGEMENT IN ACOUSTIC HEADSETS

(75) Inventor: Christer Almqvist, Skillingaryd (SE)

(73) Assignee: Peltor AB, Varnamo (SE)

( * ) Notice: Subject to any disclaimer, the term of this patent is extended or adjusted under 35 U.S.C. 154(b) by 193 days.

(21) Appl. No.: 09/501,970

(22) Filed: Feb. 10, 2000

(65) Prior Publication Data

US 2002/0080987 A1    Jun. 27, 2002

Related U.S. Application Data

(63) Continuation of application No. PCT/SE98/01459, filed on Aug. 12, 1998.

(30) Foreign Application Priority Data

Aug. 15, 1997  (SE) .................................... 9702947

(51) Int. Cl.[7] .............................................. H04L 25/00
(52) U.S. Cl. ................................... 381/371; 381/384
(58) Field of Search ................................ 381/370, 371, 381/372, 373, 374, 375; 379/430, 433, 433.06, 379/433.07, 368; 455/66, 468, 469, 25, 62

(56) References Cited

U.S. PATENT DOCUMENTS

| | | | |
|---|---|---|---|
| 4,620,068 A | * | 10/1986 | Wieder |
| 5,113,428 A | * | 5/1992 | Fitzgerald ..................... 379/61 |
| 5,619,477 A | * | 4/1997 | Schenk ........................ 368/10 |
| 5,794,127 A | * | 8/1998 | Lansang |
| 5,798,922 A | * | 8/1998 | Wood et al. ........... 364/400.01 |
| 5,923,317 A | * | 7/1999 | Sayler et al. ............... 345/156 |
| 6,091,832 A | * | 7/2000 | Shurman et al. ........... 381/381 |
| 6,310,609 B1 | * | 10/2001 | Morgenthaler |

FOREIGN PATENT DOCUMENTS

| | | |
|---|---|---|
| CA | 2180036 | 1/1997 |
| DE | 29708128 U1 | 9/1997 |
| GB | 2226931 | 7/1990 |

OTHER PUBLICATIONS

"REACT" Helleberg Safety AB, Lerum, Printed Dec. 9, 1996.

* cited by examiner

Primary Examiner—Sinh Tran
(74) Attorney, Agent, or Firm—Bachman & LaPointe, P.C.

(57) ABSTRACT

The disclosure relates to an arrangement in hearing protection, in the form of an acoustic headset, comprising a first auditory cup (10), a second auditory cup (11) and a stirrup or headband (12) interconnecting the auditory cups (10, 11), a microphone (13) being provided for receiving ambient sound and an electronic control unit (15) actuable by means of a button set (14) being provided for transmitting sound from the microphone (13) and a radio unit (16) by the intermediary of loudspeakers (17) in the auditory cups (10, 11). The button set (14) comprises a plurality of associated buttons (18, 18', 19, 19', 20, 20', 21, 22) arranged in groups, and each group of buttons being disposed, for actuation by the wearer's fingers, in a separate depression or recess (23, 24, 25, 26) in the first auditory cup (10).

5 Claims, 3 Drawing Sheets

ARRANGEMENT IN ACOUSTIC HEADSETS

CROSS-REFERENCE TO RELATED APPLICATIONS

This application is a continuation of co-pending International Application No. PCT/SE98/01459 filed Aug. 12, 1998 which designated the United States.

TECHNICAL FIELD

The present invention relates to an arrangement in hearing protection in the form of an acoustic headset, comprising a first auditory cup, a second auditory cup and a headband interconnecting the auditory cups, a microphone being provided for receiving ambient sound, and an electronic control unit actuable by a button set being provided for transmitting sound from the microphone and a radio unit by the intermediary of loudspeakers in the auditory cups.

BACKGROUND ART

Hearing protection in the form of two cups interconnected by a headband or stirrup or the like have long been employed. As electronic equipment has assumed steadily smaller dimensions, various electronic functions have also been integrated into the hearing protection. For example, it is a common occurrence that such hearing protection includes a radio, both some form of message radio and a broadcasting radio, for example on the FM wavelength. The radio sound is transmitted by the intermediary of loudspeakers integrated in the hearing protection headset.

Hearing protection systems have also been developed which include electronic amplification of the ambient sound. Reception of ambient sound is effected by means of microphones and the sound may be amplified or damped, respectively, by electronic means before being transmitted to the wearer of the headset via loudspeakers.

In a working environment at a steadily increasing tempo, the demands on protective equipment and the like have been raised. For example, it is important that hearing protection be employed in the correct manner, such that safety is not impaired. However, improvements to safety must not be put into effect at the expense of user friendliness.

OUTLINE OF THE INVENTION

One object of the present invention is to realize hearing protection of the above-described type, in which user friendliness has been developed at the same time as safety has been improved. This object is attained in that the present invention [has been given the characterizing features as set forth in appended claim 1].

Further advantages and characterizing features of the present invention will be apparent from the appended description, Drawings and appended subclaims.

BRIEF DESCRIPTION OF THE ACCOMPANYING DRAWINGS

The present invention will now be described in greater detail hereinbelow, with the aid of various embodiments and with reference to the accompanying Drawings, in which.

DESCRIPTION OF PREFERRED EMBODIMENTS

Figure 1:
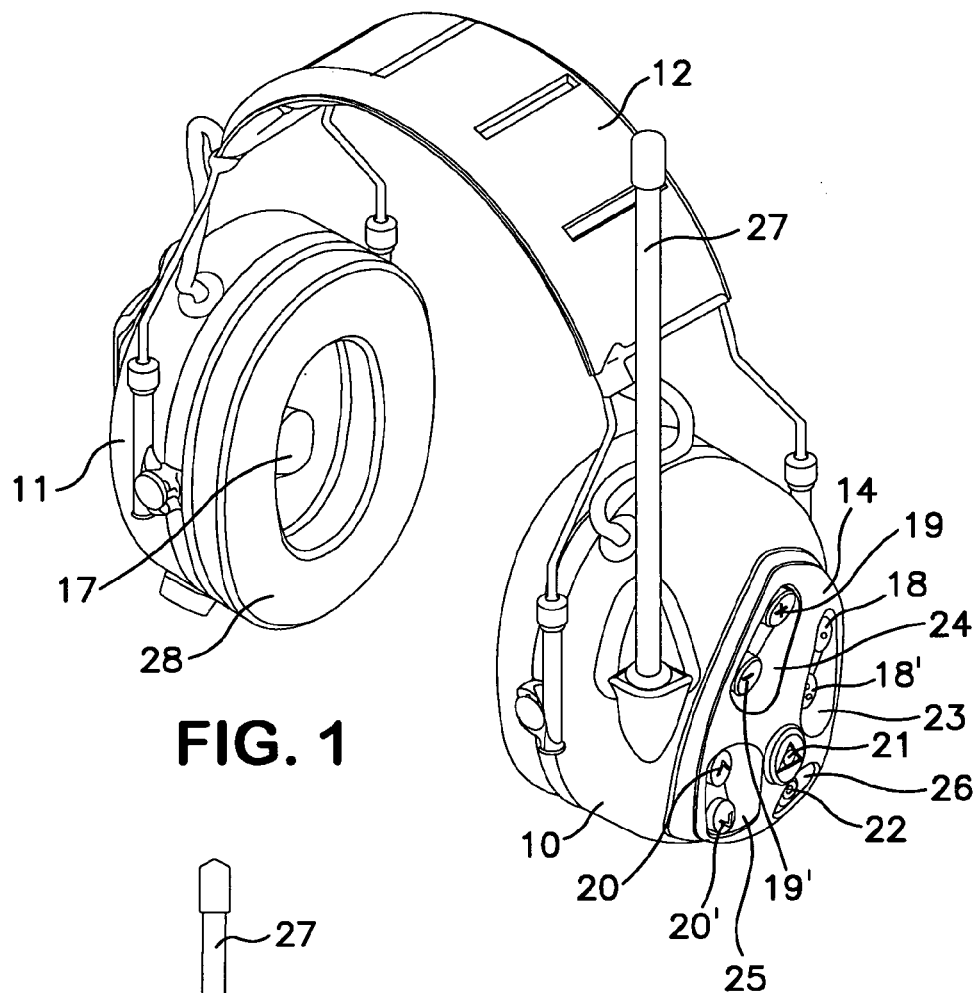
FIG. 1 is a perspective view of one embodiment of an arrangement according to the present invention, with two auditory cups.

In the embodiment according to FIG. 1, a first auditory cup 10 is connected to a second auditory cup 11 by means of a stirrup or headband 12 in a conventional manner. The first auditory cup 10 includes a button set 14 with a plurality of buttons 18, 18'; 19, 19'; 20, 20'; 21; 22 arranged in groups with associated buttons. The various buttons are connected to a control unit 15 (see FIG. 2). Each group of buttons is disposed in depressions 23, 24, 25, 26 in an arched outer side of the first auditory cup 10. FIG. 1 also shows an antenna 27 which is employed for receiving radio signals. A more detailed description of the function of the various buttons is given below with reference to FIG. 2.

The auditory cups 10, 11 are provided with cushions 28 which are intended to abut around the ears of the wearer of the headset. The cushions 28 contribute in the capability of the auditory cups substantially entirely to damp the immediate ambient sound. Within the auditory cups 10, 11, loudspeaker elements 17 are provided so that sound which is transmitted electronically according to the following description may be perceived by the wearer.

Figure 2:
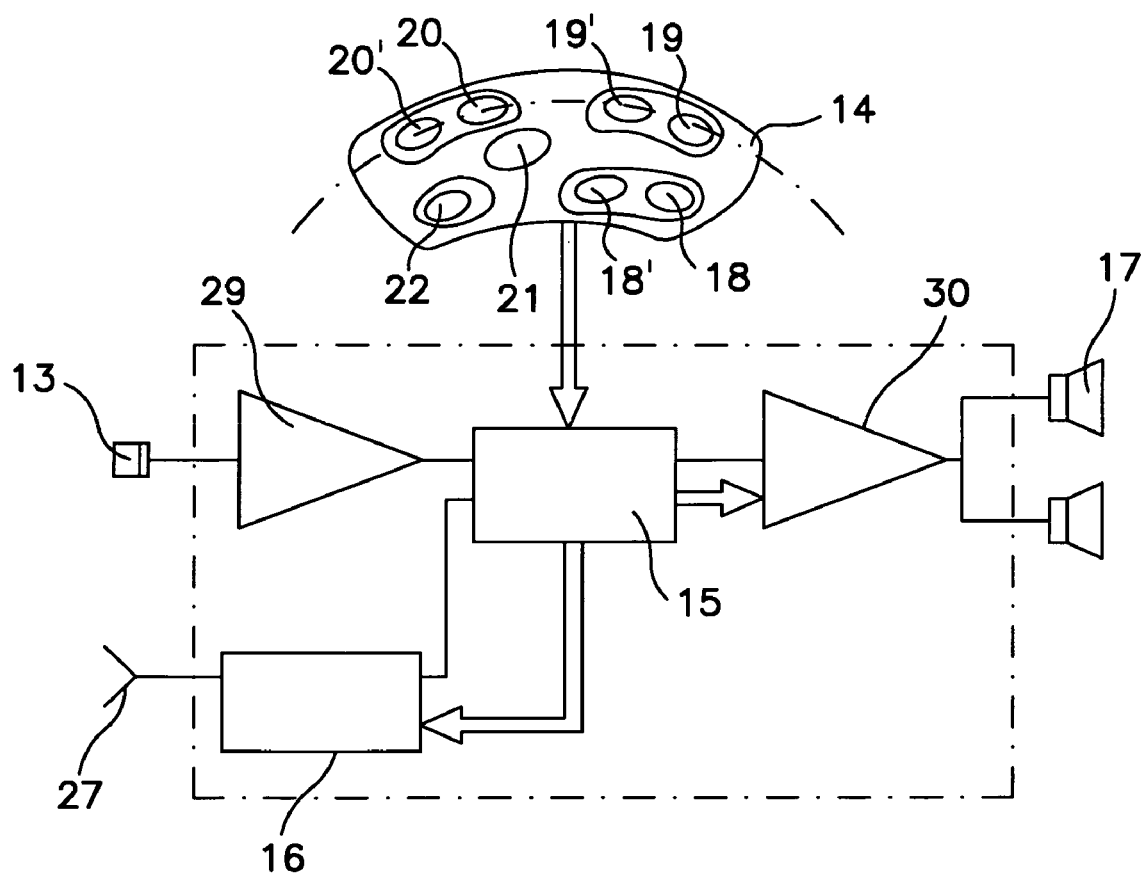
FIG. 2 is a block diagram illustration functional blocks in an electronic unit associated with the arrangement according to FIG. 1.

As will be apparent from FIG. 2, the button set 14 and the buttons included therein are connected to the control unit 15. Using a first group of buttons 18, 18', the wearer of the headset arrangement according to the present invention can influence the balance of the output signal between different sound sources. A first sound source includes a microphone 13 which is physically disposed on one or both of the auditory cups 10, 11 and which, by the intermediary of a first amplifier 29, is electrically connected to the control unit 15. A second sound source consists of a radio unit 16 with an antenna 27. The radio unit 16 is electrically connected to the control unit 15. After adjustment of the balance using the first group of buttons 18, 18' which are functionally connected to influence balance, the output signal is led from the control unit 15 by the intermediary of a second amplifier 30 to loudspeakers 17 in the auditory cups. The sound from the radio unit 16 and the microphone 13 may also be shut off using a first separate button 21. The control unit 15 is designed such that a brief depression of the first separate button 21 shuts off the radio unit 16. A more lengthy depression of the first separate button 21 shuts off the sound from remaining sound sources as well. When the equipment is activated, a first depression of the button 21 entails that the ambient sound from the microphone 13 is turned on. A second depression of the button will result in the radio sound also being turned on.

For adjusting the sound volume in the loudspeakers 17, a second group of buttons 19, 19' which are functionally connected for volume control is provided in the button set 14. The sound volume can also be adjusted independently of the balance between the different sound sources. The radio unit 16 is adjustable to different frequencies. In one particular embodiment, the radio unit 16 includes receivers for both conventional broadcast radio and company-linked radio, for example some form of communication radio. Adjustment of the radio unit 16 is put into effect with the aid of a third group of buttons 20, 20' which are functionally connected for channel searching, and a second separate button 22 for storing channels.

Figure 3:
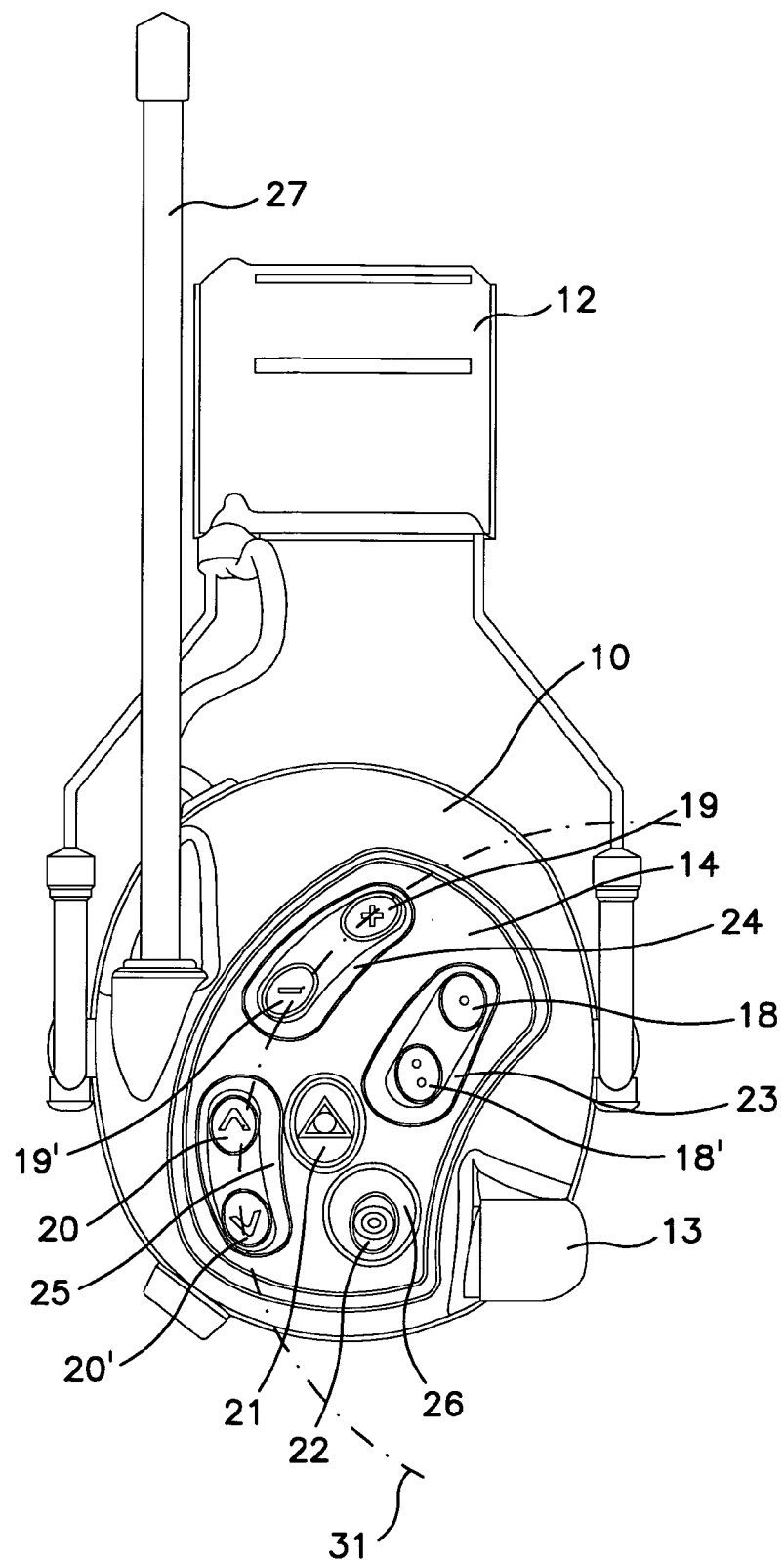
FIG. 3 is a side elevation of a first auditory cup in the arrangement of FIG. 1.

FIG. 3 shows the outside of the first auditory cup 10, with the button set 14. The button set 14 is disposed in an arched portion in which a first depression, or recess, 23 is provided for the first group of buttons 18, 18'. A similar, second depression or recess 24 is provided for the second group of buttons 19, 19', and a similar third depression or recess 25 for the third group of buttons 20, 20'. The different buttons in the button set 14 are provided with relief symbols which are unique to each respective button and function. The symbols may be recessed as a groove or project in the form of ridges or the like.

The buttons in the button set 14, above all the button groups, are disposed along circular lines 31 or the like, so that the fingers of one hand of the wearer laid over the button set fall over several of the buttons. As a result, for example the balance between the sound sources may conveniently be adjusted in the above-described manner using, for example, the index finger and the middle finger. The wearer of the headset will readily recognise the different groups of buttons, since the buttons are disposed pairwise in separate depressions or recesses and are provided with the symbols which can be felt by the wearer's fingers. The second separate button 22 is disposed in a fourth depression or recess 26. As a result, this will also be easy to identify and distinguish from the first separate button 21 which, instead, is slightly raised.

FIG. 3 shows the first auditory cup 10 which, in a normal embodiment, constitutes the right-hand auditory cup. The various buttons will, as a result, be easily accessible to the wearer's right hand. A microphone 13 is provided forwardly on the auditory cup 10, and one preferably in the same manner on the second auditory cup 11. This placing of the microphones makes for the reception of sound, above all from in front of the wearer.

Figure 4:
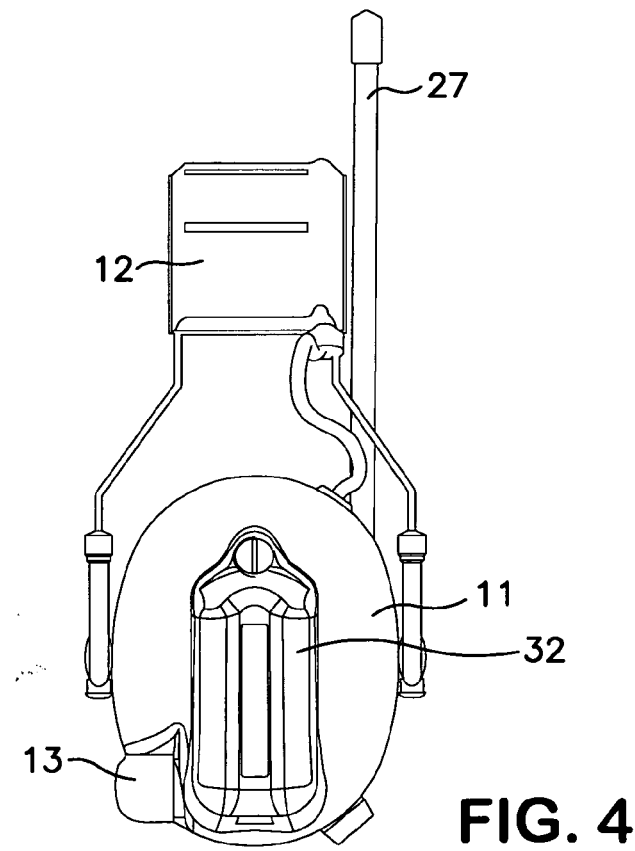
FIG. 4 is a side elevation of a second auditory cup in the arrangement of FIG. 1.

FIG. 4 shows the second auditory cup 11 which, in accordance with the foregoing, normally constitutes the left-hand auditory cup. A microphone 13 is also provided on this auditory cup in the same manner as described above. The space which, in the first auditory cup 10, is employed for the button set, and preferably for the different electronic units, is here utilised for a battery unit, of which a lid 32 is visible in FIG. 4.

The present invention should not be considered as restricted to that described above and shown on the Drawings, many modifications being conceivable without departing from the scope of the appended claims.

What is claimed is:

1. An arrangement in hearing protection in the form of an acoustic headset, comprising a first auditory cup (10), a second auditory cup (11) and a stirrup or headband (12) interconnecting the auditory cups (10, 11), a microphone (13) being provided for receiving ambient sound, and an electronic control unit (15) actuable by a button set (14) being provided for transmitting sound from the microphone (13) and a radio unit (16) by the intermediary of loudspeakers (17) in the auditory cups (10, 11), characterized in that the button set (14) comprises a plurality of associated buttons (18, 18'; 19, 19'; 20, 20'; 21; 22) arranged in groups; and that each group of buttons, for activation by means of the fingers of the wearer, is disposed in a separate depression or recess (23, 24, 25, 26) in the first auditory cup (10) wherein the depressions or recesses (23, 24, 25, 26) are disposed in an arched surface on the first auditory cup (10), and wherein at least the depressions or recesses displaying a plurality of buttons, together with the buttons disposed therein, are disposed along a curved path adapted to the length of the wearer's fingers.

2. The arrangement as claimed in claim 1, wherein a first group of buttons (18, 18') is connected to the control unit (15) for adjusting the volume relationship between sound from the radio unit (16) and sound from the microphone (13), and wherein the control unit (15) is designed to permit limited reduction of the sound from the microphone (13) to a lowest level audible to the wearer.

3. The arrangement as claimed in claim 1, wherein the buttons (18, 18'; 19, 19'; 20, 20'; 21; 22) are provided with symbols in relief indicating the function of the buttons.

4. The arrangement as claimed in claim 2, wherein a first separate button (21) is connected to the control unit (15) for shutting off sound from the radio unit (16) and the microphone (13), respectively, and wherein the control unit (15) is operative, on a brief depression of the first separate button (21), to shut off sound from the radio unit (16) and, on a more lengthy depression, to shut off sound from both the radio unit (16) and the microphone (13).

5. A hearing protection in the form of an acoustic head set comprising:
   one first and one second ear cup interconnected by a stirrup,
   one loudspeaker in each one of the ear cups,
   one microphone for receiving ambient sound,
   one radio unit, and
   one electronic control unit actuable by a button set for transmitting sound to the ear cups from the microphone and the radio unit by the intermediary of the loudspeakers, the buttons of the button set being arranged in a common recess in the first ear cup, the recess and the buttons therein being disposed along a curved path adapted to the length of the wearer's fingers.

* * * * *